(12) United States Patent
Leflaive et al.

(10) Patent No.: US 6,841,714 B2
(45) Date of Patent: Jan. 11, 2005

(54) PROCESS FOR CO-PRODUCTION OF PARAXYLENE, METAXYLENE AND/OR ORTHOXYLENE

(75) Inventors: Philibert Leflaive, Bures sur Yvette (FR); Luc Wolff, Lyons (FR); Gérard Hotier, Rueil Malmaison (FR); Alain Methivier, Marly le Roi (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 286 days.

(21) Appl. No.: 10/247,830

(22) Filed: Sep. 20, 2002

(65) Prior Publication Data
US 2003/0069461 A1 Apr. 10, 2003

(30) Foreign Application Priority Data
Sep. 20, 2001 (FR) .............................. 01 12177

(51) Int. Cl.[7] ................................................. C07C 7/12
(52) U.S. Cl. ........................ 585/828; 585/822; 585/825; 585/812
(58) Field of Search ................................. 585/828, 822, 585/825, 812

(56) References Cited

U.S. PATENT DOCUMENTS 5,284,992 A * 2/1994 Hotier et al. ............... 585/805

FOREIGN PATENT DOCUMENTS

WO          99 64381       12/1999

* cited by examiner

Primary Examiner—Thuan Dinh Dang
(74) Attorney, Agent, or Firm—Millen, White, Zelano & Branigan, P.C.

(57) ABSTRACT

A process for co-production of paraxylene, metaxylene and/or orthoxylene from a hydrocarbon feedstock (1) that comprises [1] a separation stage of the feedstock in a simulated moving bed in a chromatographic column (9) that contains a number of beds of an adsorbent, interconnected in a loop, is described, whereby said column comprises an injection (3) of the feedstock, a draw-off (10) of an extract that consists of paraxylene and desorbent, an intermediate fraction (11) (extract or raffinate) that contains ethylbenzene, and a raffinate (12) that contains a mixture of metaxylene and orthoxylene that is virtually free of ethylbenzene and paraxylene and [2] a crystallization stage (27) of the metaxylene and/or orthoxylene fraction. Upstream from the adsorption zone and/or upstream from the crystallization zone, it is possible to distill the entering mixture to produce an orthoxylene-enriched fraction at the bottom and a metaxylene-enriched fraction at the top.

20 Claims, 1 Drawing Sheet

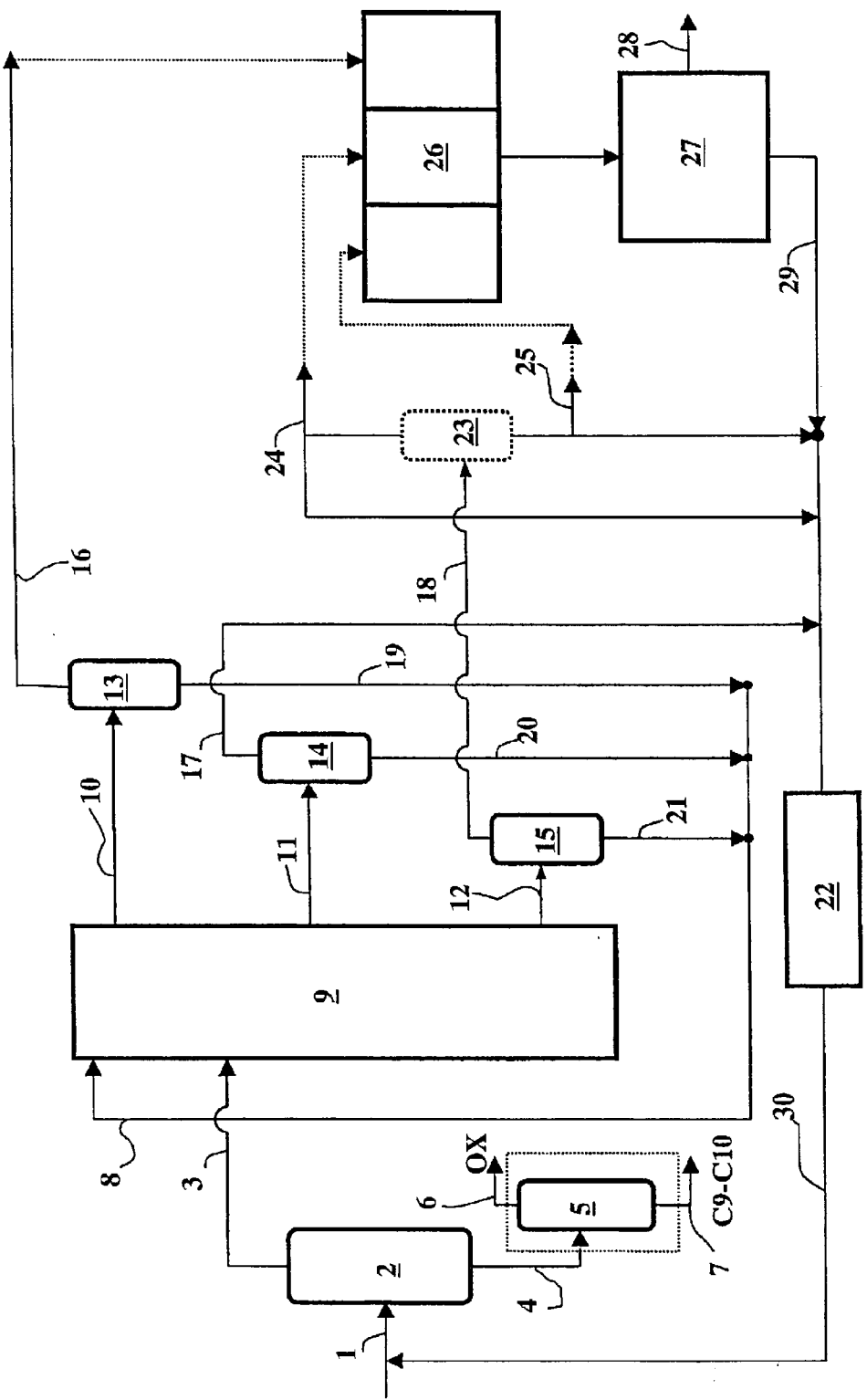

PROCESS FOR CO-PRODUCTION OF PARAXYLENE, METAXYLENE AND/OR ORTHOXYLENE

The invention relates to a process for co-production of paraxylene and metaxylene and/or orthoxylene that comprises in combination a simulated moving-bed adsorption unit and a crystallization zone.

The production of high-purity paraxylene by separation by adsorption is well known from the prior art. This market is extensively developed: its outlets are the productions of terephthalic acid, phthalic anhydride and polyethylene terephthalate resins. The technological background that describes the production of paraxylene with very high purity is illustrated in Patent EP-A-531191 of the applicant.

In contrast, the metaxylene market is still restricted, whereby its outlet is isophthalic acid. The separation of metaxylene and obtaining it at a purity level in accordance with market specifications (>99%) is the subject, however, of several processes. Thus metaxylene purification approaches from a C8 aromatic hydrocarbon feedstock have been stipulated in the prior art. Liquid-liquid extraction processes are presented in particular in U.S. Pat. Nos. 2,528,892, 2,738,372, 2,848,517, 2,848,518, 3,309,414, 3,515,768 and 3,584,068. These processes rest on stability criteria of the complex formed by bromine trifluoride ($BF_3$) and hydrofluoric acid (HF) and xylene isomers, whereby the complex that is formed with the metaxylene is the most stable. The drawback of these techniques is essentially environmental but also financial. Actually, the corrosivity and the danger associated with these products are detrimental and lead to additional costs in terms of equipment.

Other techniques for purification of metaxylene by extraction use different products but result in the same drawbacks. U.S. Pat. Nos. 2,830,105, 3,707,577, 2,562,068 thus teach respectively an extraction with phosphorus pentafluoride and hydrofluoric acid, with lithium chloride and aluminum chloride, and with sulfur dioxide and pentane.

It is also conceivable to purify metaxylene by a selective reaction followed by a separation, by halogenation as described in U.S. Pat. Nos. 2,889,382 and 3,644,552, by sulfonation (U.S. Pat. No. 2,511,711), and even by alkylation (U.S. Pat. No. 3,539,650). These processes are often expensive and involve undesirable additional products.

The extractive distillation processes, shown in U.S. Pat. No. 2,763,604 (extractive distillation with benzonitrile), U.S. Pat. No. 3,089,829 (benzoic acid) and U.S. Pat. No. 3,849,261 (organometallic compounds) exhibit a risk of contaminating products and produce considerable additional costs.

Processes for separating metaxylene by adsorption are presented in U.S. Pat. No. 4,326,092, U.S. Pat. No. 5,382,747, U.S. Pat. No. 5,900,523, which use as adsorbent a sodium-exchanged Y zeolite or a sodium- and lithium-exchanged Y zeolite and which use as desorbents indane or toluene. U.S. Pat. No. 6,137,024 describes a process for separating metaxylene from a mixture that contains the three xylenes (plus optionally ethylbenzene and/or C9 and C10 aromatic compounds) by contact with an Hβ zeolite. This process can use a desorbent that is preferably benzene, toluene or a combination of these two compounds.

Another method for purifying metaxylene is the use of the crystallization technology without tying it to a separation by adsorption. Such techniques that combine crystallization units in a series are described in U.S. Pat. No. 2,884,470 and U.S. Pat. No. 2,777,888. These processes are based on a preferential crystallization that makes it possible to avoid the problems linked to the eutectic.

A variant of this approach is the process that is disclosed in U.S. Pat. No. 3,277,200, where the co-crystallization of metaxylene and paraxylene is followed by a selective melting of paraxylene crystals to separate them from metaxylene. The scope of this process, however, is restricted to feedstocks that enter the crystallization stage containing at most 3% ethylbenzene and at most 3% orthoxylene. In U.S. Pat. No. 3,544,646, the co-crystallization of metaxylene and paraxylene is followed by a separation between the metaxylene and the paraxylene based on the density of the crystals. The proximity of the densities (respectively 1.030 g/ml and 1.006 g/ml), however, leads to doubts on the practical implementation of this operation in a commercial optical system. A similar patent, U.S. Pat. No. 3,825,614, presents a co-crystallization followed by a separation by crystal density, but the feedstock that enters this stage is substantially freed of orthoxylene thanks to an upstream orthoxylene distillation (splitter). The orthoxylene is then sent to an isomerization unit.

It now becomes advantageous to co-produce paraxylene and metaxylene in the same complex for production of aromatic compounds. Actually, it recently became evident that the addition of small amounts of polyethylene isophthalate to polyethylene terephthalate improved the properties of the latter. The market requirements call for a larger amount of paraxylene than that of metaxylene: typically 2 to 40 times larger, the paraxylene should be very pure, typically at least 99.7%, and the metaxylene should have reasonable purity, typically at least 99.0%.

The prior art also describes processes of co-production of paraxylene and metaxylene. For example, U.S. Pat. No. 4,368,347 uses a vapor phase process with intermediate fraction recycling: in addition to the complication that is linked to recycling intermediate fractions, this document does not describe and does not suggest how it is possible to use in a practical way such a process that operates at a pressure of between 1 and 2 bar and at a temperature of 150° C. to 200° C. with a feedstock whose bubble point is 145° C. and with fixed beds that have pressure drops of at least 0.1 bar and probably more to operate economically. Patent FR 2 651 148 uses two different solvents to separate the C8-aromatic fraction into three effluents, which greatly limits its scope since the distillations that result from the simulated moving bed separation unit are multiplied. Patent WO 93/22022 describes various cases of separations of feedstocks of three components into three effluents, however the technology that is used that involves very high pressures, pressure regulation and flow rate regulation at the same time in each of the three or four zones of the process and beds that are each separated in a column is justified economically only for products of very high added value.

U.S. Pat. No. 4,306,107 describes a simulated moving-bed process in liquid phase where the metaxylene is sampled in the form of extract; the paraxylene, orthoxylene and a fraction of ethylbenzene are sampled as an intermediate raffinate; and finally the ethylbenzene is sampled as a raffinate. This process that allows the co-production of metaxylene and ethylbenzene naturally does not allow a majority of paraxylene and an accompanying stream of metaxylene to be co-produced.

U.S. Pat. No. 4,313,015 describes a process for continuous co-production of paraxylene and metaxylene from a hydrocarbon feedstock in a simulated moving bed in liquid phase that comprises three samplings. The extract consists of paraxylene that is too impure (99.44%) to be marketed at current standards (current standard=99.7% minimum) and with a yield of 97.5%; the intermediate raffinate consists of ethylbenzene, orthoxylene, metaxylene and a little paraxylene; finally the raffinate consists primarily of a mixture of orthoxylene and metaxylene. Virtually pure metaxylene is then obtained by distillation of the raffinate.

A process for co-production of paraxylene and metaxylene from a hydrocarbon feedstock in a simulated moving bed in liquid phase that comprises three samplings is also described in Patent FR 2 782 714. The chromatographic column that is described contains at least twenty-five beds that are distributed in five zones. At least five beds should be located in zone 3B that is between the point for draw-off of an intermediate raffinate that contains metaxylene, orthoxylene, ethylbenzene, solvent and paraxylene, and the point for draw-off of a raffinate that contains metaxylene, orthoxylene and solvent. Metaxylene with a purity that is higher than 99% is then obtained by distillation of the raffinate. In addition to the large number of beds necessary for the implementation of the process (30, for example), the hydrocarbon feedstock should have an ethylbenzene content that is less than 5%, which is restricting.

The applicant filed a patent application FR 00/05 424 that describes a process for coproduction in a simulated moving bed of paraxylene and metaxylene in a chromatographic column comprising three samplings from a non-limited feedstock of ethylbenzene where an extract that contains paraxylene is drawn off continuously, a first raffinate is drawn off continuously or intermittently, and where a second raffinate that comprises orthoxylene and metaxylene is drawn off intermittently, whereby the process is also characterized in that the second raffinate is distilled so as to recover pure orthoxylene and metaxylene.

Document U.S. Pat. No. 5,510,562 also describes a process for separation of C8 aromatic compounds where the mixture of orthoxylene, metaxylene, paraxylene and ethylbenzene is first divided into two flows that respectively contain paraxylene and ethylbenzene, and metaxylene and orthoxylene. The paraxylene is then separated from the ethylbenzene by a distillation followed by a crystallization, and the metaxylene is separated from the orthoxylene by distillation.

U.S. Pat. No. 3,700,744 describes a process for the production of paraxylene (PX), orthoxylene (OX), and metaxylene (MX) from a flow of C8 aromatic compounds by first carrying out a fractionated distillation to produce a top fraction that contains ethylbenzene (EB), PX and MX that is lacking in any OX, an intermediate fraction that contains a mixture of PX and MX, and a bottom fraction that contains essentially pure orthoxylene. The top fraction is next isomerized and then recycled in the fractionation zone. The intermediate fraction that contains the PX and the MX is sent into a separation zone by adsorption to produce essentially pure paraxylene and metaxylene. A variant of this process consists in producing paraxylene (PX), orthoxylene (OX) and metaxylene (MX) from a flow of C8 aromatic compounds by first carrying out a distillation to produce a top fraction that contains ethylbenzene (EB), PX and MX and OX, and a bottom fraction that contains a mixture of three xylenes that are lacking in EB. The top fraction is next isomerized and then recycled in the fractionation zone. The bottom fraction that contains the PX and the MX is sent into a zone for separation by adsorption to produce essentially pure paraxylene or metaxylene in an extract and a raffinate that contains a mixture of orthoxylene and the least well-retained compound of paraxylene or metaxylene. The raffinate is then distilled to produce essentially pure metaxylene and orthoxylene.

In all of the processes that are described in U.S. Pat. No. 4,313,015, FR 2 782 714, U.S. Pat. No. 5,510,562 and U.S. Pat. No. 3,700,744 as well as in Patent Application FR 00/05 424, high-purity metaxylene (>99%) is obtained by distillation. The boiling points of these two compounds, however, are very close (i.e., respectively 139.12° C. and 144.41° C.), which makes it very difficult to obtain high-purity metaxylene by distillation and requires a large column with at least 150 to 200 plates and a very high reflux rate, typically a reflux to feedstock ratio that is higher than 5 to 1. In addition, if the metaxylene and orthoxylene mixture flow that it is sought to separate contains impurities in the form of paraxylene and ethylbenzene, these impurities will be concentrated in the metaxylene, making it difficult to obtain a purity that is higher than 99.0%.

In Example E, U.S. Pat. No. 5,900,523 describes a process for the production of xylenes where a first zone for separation by paraselective adsorption produces a paraxylene-enriched extract and a raffinate that comprises at least the majority of orthoxylene and metaxylene that are present in the feed flow and that contains more than 10 percent of orthoxylene. The extract is distilled to recover high-purity paraxylene. The raffinate of the first separation zone is then introduced into a second separation zone by metaselective adsorption where the adsorbent is a Y zeolite with an $SiO_2/Al_2O_3$ molar ratio of between 4.0 and 6.0 that is exchanged with sodium and that has a water content that is equivalent to a fire loss at 500° C. from about 1.5 to about 2.5% by weight; the separation is conducted in a liquid phase at a temperature of between 100° C. and 150° C. The second zone of separation by metaselective adsorption produces a metaxylene-enriched extract and a raffinate that comprises the non-adsorbed compounds of the first raffinate, in particular orthoxylene. High-purity metaxylene is recovered from the extract.

The two patents that are closest to this invention are U.S. Pat. No. 3,773,846 and WO 99/64381. U.S. Pat. No. 3,773,846 as well as the patents described below thus propose the linking of a paraxylene production unit and purification of metaxylene by adsorption or crystallization, and optionally an isomerization unit. U.S. Pat. No. 3,798,282 and U.S. Pat. No. 3,825,614 present metaxylene crystallization methods downstream from a paraxylene crystallization unit. The crystallization techniques that are used allow a coarse separation of metaxylene crystals that are larger than the paraxylene crystals. After this first separation, the concentrated metaxylene can be melted and recrystallized in a second stage to produce high-purity metaxylene. U.S. Pat. No. 3,773,846 shows the advantage of an adsorption stage prior to the crystallization to reduce the paraxylene concentration in the metaxylene crystallization unit. It claims a simultaneous production process of high-purity metaxylene and high-purity paraxylene from a fresh feedstock of C8 aromatic hydrocarbons. The first zone is a selective adsorption zone that produces a high-purity paraxylene flow and a paraxylene-depleted flow at a concentration that is below the eutectic binary metaxylene-paraxylene. A fractionation stage of this depleted flow makes it possible to produce at the top a mixture of metaxylene and orthoxylene, whereby the latter is in a proportion smaller than that of the eutectic mixture. This mixture is introduced into a crystallization unit that makes it possible to produce a high-purity metaxylene flow and a mother liquor. The fractions that are collected at the bottom of the fractionation column and the mother liquor of the crystallization are recycled in an isomerization zone to produce a mixture of C8 aromatic hydrocarbons in conditions close to the thermodynamic equilibrium. The fresh feedstock can be introduced directly into the selective adsorption zone or into the isomerization zone before the adsorption stage.

Likewise, Patent WO 99/64381 uses the crystallization as a metaxylene separation technique. The first stage for separation of paraxylene and metaxylene from the feedstock of C8 aromatic compounds is done by simulated moving-bed adsorption after the feedstock passes into a distillation column that produces at the bottom an orthoxylene-rich flow and a distillate that contains for the most part ethylbenzene, paraxylene and metaxylene. As a result, the composition of the mixture and in particular the paraxylene content is modified by the adsorption stage, which affects the crystallization and induces a different design of crystallization units. The crystallization stage exhibits several variants, structured around successive crystallizations below the eutectic point, with or without a crystallization drum. This patent proposes several methods for separating orthoxylene and uses a transalkylation unit rather than an isomerization unit to isomerize the recycled orthoxylene.

A common point in U.S. Pat. No. 3,773,846 and WO 99/64381 is the presence of ethylbenzene in the raffinate that is drawn off from the adsorption unit. U.S. Pat. No. 3,773,846, moreover, notes this drawback by proposing a distillation that makes it possible to deplete of ethylbenzene the flow that enters into the crystallization unit. In Patent WO 99/64381, the ethylbenzene is sent directly into the crystallization unit, which needlessly increases the entering flow.

This invention has as its object to eliminate the above-mentioned drawbacks.

The object of the invention is the co-production of paraxylene and metaxylene and/or orthoxylene that can be marketed from a hydrocarbon feedstock. The main object of the invention is to obtain paraxylene with a purity of at least 99.7%. The second object of the invention is to produce about 10 to 15 times less metaxylene than paraxylene but with a purity that is at least equal to 99% and/or orthoxylene with a purity that is at least equal to 98.5%.

More specifically, the invention relates to a process for co-production of paraxylene and metaxylene and/or orthoxylene from a feedstock that contains xylenes, ethylbenzene and C9–C10 hydrocarbons, whereby the process successively comprises:

A passage of feedstock (1) in a column for distillation of xylenes (2) from where a mixture (3) that comprises the majority of metaxylene, paraxylene, ethylbenzene and at least a portion of orthoxylene is drawn off at the top, and from where a flow (4) of C9"C10 hydrocarbons and the remaining portion of orthoxylene is drawn off at the bottom;

A separation of top mixture (3) in a simulated moving bed in at least one chromatographic column (9) containing a number of beds of an adsorbent that are interconnected in a closed loop and having a different selectivity for paraxylene, ethylbenzene, metaxylene and orthoxylene, whereby said column comprises at least five zones that are delimited by injections of mixture (3) (adsorption feedstock) and a desorbent (8) and draw-offs of an extract (10) that contains paraxylene, an intermediate fraction (11) that contains ethylbenzene, a raffinate (R2) (12) that contains orthoxylene and metaxylene, whereby a paraxylene desorption zone 1 is included between the injection of the desorbent and the sampling of the extract, whereby a zone 2 for desorption of ethylbenzene, orthoxylene and metaxylene is included between the sampling of the extract and the injection of the adsorption feedstock, whereby a zone 3A for paraxylene adsorption is included between the injection of the feedstock and the draw-off of the intermediate fraction, whereby a zone 3B for ethylbenzene adsorption is included between the draw-off of the intermediate fraction and the draw-off of raffinate (R2), and whereby a zone 4 is included between the draw-off of raffinate (R2) and the injection of desorbent, whereby the process is characterized in that:

Raffinate (2) is distilled to eliminate essentially all of the desorbent, and a distilled raffinate (18) is drawn off, The extract is distilled to recover a paraxylene-enriched fraction (16).

The process is also characterized in that:

Either distilled raffinate (18) is sent at least in part to at least one crystallization zone (27), and metaxylene with a purity of at least 99% is recovered, Or distilled raffinate (18) is sent at least in part into a second distillation zone (23), a top flow (24) that contains metaxylene and a bottom fraction (25) that contains orthoxylene are recovered, the top flow is crystallized at least in part, metaxylene with a purity of at least 99% is recovered, and/or said bottom fraction is crystallized at least in part, and orthoxylene with a purity of at least 98.5% is recovered.

The stage for separation of paraxylene and metaxylene is done by a simulated moving-bed adsorption from where are drawn off an extract that comprises paraxylene and desorbent, an intermediate fraction (extract or raffinate) that contains ethylbenzene with a strong yield, and a raffinate that contains a mixture of metaxylene and orthoxylene that is virtually free of ethylbenzene and paraxylene. The draw-off of an ethylbenzene-rich intermediate fraction makes the presence of ethylbenzene splitter superfluous. Actually, the feedstock that enters the crystallization zone is virtually free of ethylbenzene, which makes possible the reduction of the entering flow and an optimized operation of the unit.

The crystallization of the metaxylene and/or orthoxylene fraction can be carried out in one or more stages and is in general conducted so as to obtain a preferred final purity of at least 99.0%, whereby the yield of metaxylene or orthoxylene relative to the feedstock can be adapted to a value of 3 to 30%.

On the other hand, it is possible to choose a unit that typically comprises 24 beds in the case, for example, of a unit revamping. Preferably, in the case of a new unit, the configuration can use 26 or 28 beds.

The chromatographic column that operates in simulated countercurrent or in simulated co-current can preferably comprise at least 24 beds and at least three beds in zone 3B.

The feedstock can have a content of linear and branched alkanes and naphthenes that is less than 1% by weight and advantageously a naphthene content that is less than 0.3%. The feedstock in general contains less than 10% by weight of ethylbenzene. It can come from either a unit for transalkylation of C7 and C9 into xylenes or from a unit for catalytic dismutation of toluene into benzene and xylenes, or from a unit for isomerization of a fluid that contains ethylbenzene, whereby said unit can be operated in the presence of a catalyst that dealkylates ethylbenzene into benzene as described in U.S. Pat. No. 5,516,656 and WO 98/05 613.

During the first simulated moving-bed separation stage, the intermediate fraction and raffinate (R2) can be drawn off continuously or intermittently. By drawing off the raffinate preferably continuously, it is possible to inject it continuously in the desorbent distillation stage, without an intermediate buffer tank.

According to a characteristic of the process, it is possible to initiate the purification by crystallization of the extract from which desorbent was previously removed by distillation. This crystallization will preferably be conducted between +10° C. and −30° C. as described in, for example, Patent EP 531 191-B1. The mother liquor that is obtained from the crystallization can then be recycled at the feed of the simulated moving-bed chromatography. The solvent for washing paraxylene crystals that are obtained is selected, for example, from among the following solvents: n-pentane, water, purified paraxylene or toluene, and the washing liquor that results from the washing stage can be recycled in the feed of the adsorption column in a simulated moving bed.

According to a characteristic of the process, mixture (4) of orthoxylene and C9–C10 aromatic hydrocarbons drawn off at the bottom of distillation column (2) can be sent into another distillation column (5), from where a high-purity (at least 98.5%) orthoxylene flow (6) is extracted at the top, and a flow (7) that contains C9–C10 hydrocarbons is extracted at the bottom. Flow (3) that is drawn off at the top of the distillation column that is placed upstream from the adsorption unit usually contains less than 5% by weight of orthoxylene. While the amount of orthoxylene that enters the first stage for separation of paraxylene by adsorption is considerably lower, its content in raffinate (R2) is reduced, and the metaxylene crystallization yield is thereby improved.

According to one of two variants for the process, raffinate (R2) from which the desorbent is removed can be sent at least in part to a second distillation column (23) from where an orthoxylene-enriched flow (25) is drawn off at the bottom, and a metaxylene-enriched flow (24) that feeds crystallization zone (27) is drawn off at the top. In the case where little or no orthoxylene is desired to be produced, this distillation is thus localized advantageously between the simulated moving-bed unit and the crystallization zone. A partial distillation is then sufficient to obtain at the top of the column a feedstock with a sufficient metaxylene content so that the crystallization zone operates with a correct yield. The crystallization stage will make it possible to limit the number of plates and avoid high reflux and reboiling rates, contrary to U.S. Pat. No. 4,313,015, FR 2 782 714 and U.S. Pat. No. 5,510,562 where the purification of the metaxylene requires a large column with at least about 150 to 200 plates.

According to a characteristic of the invention, at least a portion of the orthoxylene-enriched flow that exits from second column (25) can be isomerized in at least one isomerization zone, and the isomerate that is obtained is recycled in distillation column (2).

According to another characteristic of the process, the adsorbent that is used in the first separation stage can comprise an X zeolite that is exchanged with barium or a Y zeolite that is exchanged with potassium or a Y zeolite that is exchanged with barium and potassium.

The preferred desorbent is paradiethylbenzene, however other desorbents such as toluene, paradifluorobenzene or diethylbenzenes in a mixture can also be suitable.

According to another characteristic of the invention, the volumetric ratio of desorbent to feedstock in the first separation stage can be between 0.5 and 2.5, preferably between 1.4 and 1.7.

According to another characteristic of the invention, it is possible to carry out the first stage of the process at a temperature that is generally between 20° C. and 250° C., preferably between 90° C. and 210° C., and more particularly between 160° C. and 200° C. and under a pressure that is between the bubble pressure of xylenes at the operating temperature and 20 bar (1 bar=0.1 MPa).

According to a preferred characteristic of the invention, for the production of metaxylene, it is possible to regulate the flow rates of zones 3A and 3B as well as the optional distillation of orthoxylene in column (2) and/or second column (23) to obtain as a crystallization feedstock an effluent that is virtually free of ethylbenzene and desorbent and a molar composition that is delimited by the four points: pure metaxylene, eutectic binary metaxylene-paraxylene (metaxylene 87.0%, paraxylene 13.0%), eutectic ternary meta-ortho-paraxylene (metaxylene 61.4%, orthoxylene 30.5%, paraxylene 8.1%), and eutectic binary meta-orthoxylene (metaxylene 66%, orthoxylene 33.4%).

According to an embodiment of the process, line (24) that is drawn off at the top of the column and line (25) that is drawn off at the bottom of column (23) are generally connected at the inlet of one or more crystallization batch vat(s) (26). Line (16) of paraxylene with a purity of at least 99.7% can also feed, in a restricted amount, a crystallization batch vat so as to obtain paraxylene of very high purity. The objective of using these batch vats is to make it possible for each to produce isomers in runs, by obtaining, after passage in crystallization zone (27), a purified flow (28) that comprises either metaxylene with at least 99.0%, or orthoxylene with at least 98.5%, or ultra-pure paraxylene with at least 99.90% and, for example, greater than 99.95%.

According to a variant embodiment, the crystallization of metaxylene and that of orthoxylene can be carried out in a single crystallization zone, in runs, to produce metaxylene and orthoxylene separately.

According to another variant, the crystallization of the metaxylene and that of orthoxylene can be carried out in different crystallization zones.

For the production of orthoxylene by crystallization, it is possible to regulate the flow rates of zones 3A and 3B, as well as the optional distillation of orthoxylene in column (2) and/or column (23) to obtain as crystallization feedstock an effluent that is essentially free of ethylbenzene and desorbent and a molar composition that is delimited by the four points: pure orthoxylene, eutectic binary orthoxylene-paraxylene (orthoxylene 75.7%, paraxylene 24.3%), eutectic ternary meta-ortho-paraxylene (metaxylene 61.4%, orthoxylene 30.5%, paraxylene 8.1%), and eutectic binary meta-orthoxylene (metaxylene 66.6%, orthoxylene 33.4%).

According to a preferred characteristic of the invention, the crystallization zones can consist of one or more crystallizers, for example static crystallizers that alternate between a cooling phase and a heating phase. A refrigeration unit is used to operate at a temperature of between −45° C. and −60° C. in the case where it is sought to produce metaxylene, between −20° C. and −60° C. in the case where it is sought to produce orthoxylene, and between 20° C. and −50° C. in the case where it is sought to produce paraxylene. After obtaining the desired fraction (metaxylene, orthoxylene or paraxylene), the remaining mother liquor is drawn off from the crystallizer. The purest crystalline layer continues to adhere to the static crystallizer plates. These crystals are then purified by initiating heating at a temperature that is slightly higher than the crystallization point. This partial melting and this resuspension wash the crystals and make it possible to obtain a product with a purity that is greater than 99% and greater than 99.90% for the ultra-pure paraxylene. Washing with said high-purity product or a combination of washing and a partial melting are other alternatives for the purification of crystals. Separated mother liquor (29) can then be recycled continuously in isomerization unit (22).

In the case where it is sought to produce metaxylene in the crystallization zone, it will be possible to use this known method of the prior art for the separation of metaxylene by crystallization. It is possible to cite, for example, the Sulzer Chemtec processes that are described in the journal Chemical Engineering, May 2000, and in Patents WO 99/64381 and U.S. Pat. No. 3,773,846.

According to another characteristic according to which the chromatographic column produces paraxylene, not at at least 99% purity with a low productivity, but at at least 50% purity with a high productivity, it is possible to send the thus produced fraction from which desorbent is removed into at least one crystallization zone to deliver paraxylene crystals and a mother liquor; the crystals are separated from the mother liquor, optionally resuspended, washed and recovered; and the mother liquor can be recycled at least in part in the chromatographic column.

The crystallization and the various stages of separation of the mother liquor and paraxylene purification are described in, for example, U.S. Pat. No. 6,147,272 and U.S. Pat. No. 6,111,161 of the applicant.

The crystals that are formed can be washed by suitable washing solvents; the very high-purity product is recovered, and the washing liquor that results therefrom that comprises the impurities can be recycled in the resuspension zone.

The productivity of the adsorption unit is thereby maximized by releasing purity constraints on the paraxylene that is obtained from the adsorption unit and by ensuring the final purity of this product by at least one crystallization stage. This purity can reach at least 99.6% and preferably at least 99.7%, whereby the purity of metaxylene and/or that of orthoxylene remain unchanged, however.

Furthermore, the operating costs of the adsorption unit are minimized because it is possible to operate it with a small number of beds and a low level of solvent It is actually possible to work preferably with at most 24 beds and even more particularly with 20 beds. It is also possible to minimize the amount of desorbent by injecting it into zone 1 and by injecting the feedstock into zone 3A of the column in a volumetric ratio of desorbent to feedstock of at most 1.7:1, for example in a ratio of between 0.7 and 1.5, and very advantageously between 1.2 and 1.5.

The invention will be better understood based on FIG. 1 that illustrates the co-production of paraxylene and metaxylene and/or orthoxylene continuously or intermittently in a simulated moving bed and in countercurrent, combined with a crystallization zone.

A feedstock of xylenes comprising metaxylene, orthoxylene, ethylbenzene and paraxylene is introduced continuously via a line (1) into a column (2) for distillation of xylenes from where a flow (3) that comprises metaxylene, orthoxylene, ethylbenzene and paraxylene is drawn off at the top, and a flow (4) that consists of C9–C10 compounds and a portion of orthoxylene is drawn off at the bottom. Flow (4) can be distilled in a distillation column (5) that delivers essentially pure orthoxylene at the top via a line (6) and $C_9$–$C_{10}$ hydrocarbons at the bottom via a line (7). Flow (3) is introduced continuously into at least one chromatographic column (9) with at least five zones that contain a number of beds, 24 beds for example, of an adsorbent that comprises a zeolite, an X zeolite that is exchanged with barium, for example, and that operates in a liquid phase in a simulated moving bed and in counter-current according to U.S. Pat. No. 4,313,015 and the already cited patent of the applicant. An intermediate fraction (R1) is drawn off continuously via a line (11) at a point that is located downstream from the point of introduction of the feedstock, while a raffinate (R2) that contains metaxylene and orthoxylene is drawn off continuously via a line (12) downstream from the intermediate raffinate relative to the direction of flow of fluids in the column (specifically from the bottom to the top). A desorbent, paradiethylbenzene, is injected continuously via a line (8) at a point of the column that is located upstream from the injection point of the feedstock while an extract that contains desorbent and essentially pure paraxylene is drawn off continuously via a line (10) at a point that is located downstream from the injection point of the desorbent. This extract is distilled in a distillation column (13), from which an essentially pure paraxylene (greater than 99.7%) is drawn off at the top via a line (16), and the desorbent that can be recycled in the chromatographic column is drawn off at the bottom via a line (19).

Intermediate fraction (R1) is introduced into a distillation column (14) from which the desorbent that can be recycled is drawn off at the bottom via a line (20), and a mixture that contains xylenes and ethylbenzene is drawn off at the top via a line (17) that makes it possible to send it to an isomerization unit (22).

Raffinate (R2) is introduced into a distillation column (15) from which the desorbent that can be recycled in line (8) is drawn off at the bottom via a line (21), and a mixture that contains essentially metaxylene and orthoxylene and that is virtually free of paraxylene and ethylbenzene is drawn off at the top via a line (18). This line (18) is connected to the inlet of a column for distillation of orthoxylene (23) from where a metaxylene-enriched flow (24) is drawn off at the top, and an orthoxylene-enriched flow (25) is drawn off at the bottom. Flows (24) and (25) can be recycled in an isomerization unit (22) or sent to a crystallization zone (27). The pure crystals are separated from a mother liquor and recovered via a line (28). The mother liquor that is obtained from the crystallization is sent via a line (29) into isomerization unit (22).

The isomerate that is obtained is recycled via a line (30) into line (1) for feed of the feedstock of distillation column (2).

The invention is illustrated by the following examples that are given as non-limiting.

EXAMPLE 1

The production of paraxylene from a feedstock from which hydrocarbons comprising 9 and 10 carbon atoms were previously removed and that comprises a mixture of xylenes and ethylbenzene with the following composition by weight:

EB: Ethylbenzene 5.6%

PX: Paraxylene 22.6%

MX: Metaxylene 49.9%

OX: Orthoxylene 21.9% is carried out in a simulated moving bed in counter-current.

The pilot unit that is used to do this consists of 24 columns that are 1.1 m in length and 0.021 m in diameter. 344 g of barium-exchanged X zeolite with a moisture level of 5.5%, expressed in terms of fire loss at 900° C., is loaded per column. The operating temperature is 175° C., the pressure at the intake of the recycling pump is kept at 10 bar, all of the flows are injected or drawn off continuously with the flow rate being monitored, with the exception of the intermediate raffinate that is drawn off continuously with the pressure being monitored, and the injection and draw-off flow rates are expressed in ambient conditions of pressure and at 20° C. A raffinate (R2) and an intermediate fraction R1 (intermediate raffinate) are drawn off continuously. The total number of beds is 24. Five beds are counted between the injection of desorbent and the draw-off of raffinate, 9 beds between the draw-off of extract and the injection of feedstock, 5 beds between the injection of feedstock and the draw-off of intermediate raffinate, 3 beds between the draw-off of intermediate raffinate and the draw-off of raffinate and 2 beds between the draw-off of raffinate and the injection of desorbent.

The operating conditions are as follows:
Feedstock: 3.24 l.h$^{-1}$
Solvent: 5.52 l.h$^{-1}$ of desorbent (99.06% of paradiethylbenzene and 0.94% of other $C_{10}$ aromatic hydrocarbons)
Extract: 3.27 l.h$^{-1}$
Intermediate raffinate (R1): 4.29 l.h$^{-1}$
Raffinate (R2): 1.2 l.h$^{-1}$
Recycling flow rate (in zone 1): 16.4 l.h$^{-1}$
The R2/R1 ratio is 0.28.
The switching time of the valves (or period) is 70.8 seconds.

After the paradiethylbenzene is distilled, the extract that is obtained that is drawn off continuously delivers a flow of 0.71 l/h of paraxylene with 99.7% purity.

The 1.2 l.h$^{-1}$ of raffinate is distilled, and a fluid flow rate of 0.13 l.h$^{-1}$ is obtained whose composition by weight is as follows:
EB: Ethylbenzene 0.1%
PX: Paraxylene 1.7%
MX: Metaxylene 73.9%
OX: Orthoxylene 24.2%

The crystallization zone comprises two static crystallizers that alternate between a cooling phase and a heating phase when the crystals are produced. A refrigeration unit is used to produce metaxylene crystals at −60° C. After crystallization, the mother liquor is drawn off. The metaxylene crystals are washed with very high-purity molten metaxylene and are simultaneously purified by a partial melting at −45° C.

The metaxylene yield of the crystallization is 29%.
The amount of paraxylene that is produced by the overall unit is 25 times greater than the amount of metaxylene, or respectively 0.71 l/h of paraxylene with 99.7% purity and 0.028 l/h of metaxylene with 99.0% purity.

EXAMPLE 2

Example 1 is repeated by adding a column for distillation of the orthoxylene before the crystallization zone to improve the crystallization yield.

As above, the 1.2 l.h$^{-1}$ of raffinate R2 is distilled, and a fluid flow rate of 0.13 l.h$^{-1}$ is obtained whose composition by weight is as follows:
EB: Ethylbenzene 0.1%
PX: Paraxylene 1.7%
MX: Metaxylene 73.9%
OX: Orthoxylene 24.2%

The metaxylene yield is 6%. Raffinate 2 that is free of desorbent is then sent into an orthoxylene distillation column. A fluid flow rate of 0.05 l/h is drawn off at the bottom of the column, and the composition of this fluid by weight is as follows:
PX: Paraxylene 1.2%
MX: Metaxylene 49.4%
OX: Orthoxylene 49.4%

The orthoxylene yield at the bottom of the column is 79%.
At the top of the column, the fluid that is drawn off at a rate of 0.08 l/h has a composition by weight as follows:
EB: Ethylbenzene 0.2%
PX: Paraxylene 2.1%
MX: Metaxylene 89.4%
OX: Orthoxylene 8.3%.

The flow rates that relate to the input of the distillation (splitter) and the crystallization are 1 and 0.61. The metaxylene yield of the crystallization that is produced according to that of Example 1 is 72%.

The amount of paraxylene that is produced by the global unit is 13.7 times greater than the amount of metaxylene, or respectively 0.71 l/h of paraxylene with 99.7% purity and 0.05 l/h of metaxylene with 99.0% purity.

EXAMPLE 3

The same operating conditions as in Example 2 are repeated, but the ratio of the raffinate flow rates (R2) and intermediate raffinate (R1):R2/R1 is modified. The flow rates are as follows:
Feedstock: 3.24 l.h$^{-1}$
Solvent: 5.52 l.h$^{-1}$ of desorbent (99.06% of paradiethylbenzene and 0.94% of other $C_{10}$ aromatic hydrocarbons)
Extract: 3.27 l.h$^{-1}$
Intermediate raffinate (R1): 3.45 l.h$^{-1}$
Raffinate (R2): 2.04 l.h$^{-1}$
Recycling flow rate (in zone 1): 16.4 l.h$^{-1}$
Ratio R2/R1 is 0.59.
The switching time of the valves (or period) is 70.8 seconds.

After paradiethylbenzene is distilled, the extract that is obtained and that is drawn off continuously delivers a flow of 0.71 l/h of paraxylene with 99.7% purity.

The 2.04 l.h$^{-1}$ of raffinate R2 is distilled, and a fluid flow rate of 0.39 l.h$^{-1}$ is obtained whose composition by weight is as follows:
EB: Ethylbenzene 0.07%
PX: Paraxylene 0.98%
MX: Metaxylene 69.8%
OX: Orthoxylene 29.1%

The metaxylene yield is 17%. Raffinate R2 is then sent into an orthoxylene distillation column. A fluid flow rate of 0.17 l.h is drawn off at the bottom of the column, and the composition by weight of the fluid is as follows:
PX: Paraxylene 0.8%
MX: Metaxylene 59.0%
OX: Orthoxylene 40.2%

The orthoxylene yield at the bottom of the column is 60%.
At the top of the column, the fluid that is drawn off at a rate of 0.22 l/h has the following composition by weight:
EB: Ethylbenzene 0.1%
PX: Paraxylene 1.1%
MX: Metaxylene 78.2%
OX: Orthoxylene 20.6%.

The flow rates that relate to the input of the splitter and the crystallization are 1 and 0.56. The metaxylene yield of the crystallization according to that of Example 1 is 41.5%.

The amount of paraxylene that is produced by the overall unit is 9.75 times greater than the amount of metaxylene, or respectively 0.71 l/h of paraxylene with 99.7% purity and 0.072 l/h of metaxylene with 99.0% purity.

EXAMPLE 4

This example illustrates the production of paraxylene from a feedstock from which $C_9$ and $C_{10}$ hydrocarbons are essentially removed and that comprises a mixture of xylenes and ethylbenzene that is more concentrated in ethylbenzene than in the preceding examples and that has the following composition by weight:

EB: Ethylbenzene 8.5%
PX: Paraxylene 21.1%
MX: Metaxylene 48.9%
OX: Orthoxylene 21.4%.

The separation of paraxylene is carried out in the same pilot unit as the one that is described in Example 1 and that consists of 24 beds that are 1.1 meters in length and 0.021 m in diameter and that contains a barium-exchanged X zeolite. A raffinate (raffinate 2) and an intermediate raffinate are drawn off continuously.

The operating conditions are as follows:

Feedstock: 3.24 $l.h^{-1}$

Solvent: 5.52 $l.h^{-1}$ of desorbent (99.06% of paradiethylbenzene and 0.94% of other $C_{10}$ aromatic hydrocarbons)

Extract: 3.24 $l.h^{-1}$

Intermediate raffinate (R1): 4.11 $l.h^{-1}$

Raffinate (R2): 1.41 $l.h^{-1}$

Recycling flow rate (in zone 1): 16.4 $l.h^{-1}$

The configuration is 5 beds, 9 beds, 5 beds, 3 beds and 2 beds respectively in zones 1, 2, 3A, 3B and 4.

The ratio R2/R1 is 0.34.

The switching time of the valves (or period) is 70.8 seconds.

After the paradiethylbenzene is distilled, the extract that is obtained and that is drawn off continuously delivers a flow of 0.66 l/h of paraxylene with 99.7% purity.

The 1.41 $l.h^{-1}$ of raffinate is distilled, and a fluid flow rate of 0.19 $l.h^{-1}$ is obtained whose composition by weight is as follows:

EB: Ethylbenzene 0.2%
PX: Paraxylene 1.4%
MX: Metaxylene 70.2%
OX: Orthoxylene 28.2%

The metaxylene yield is 8.6%. Raffinate 2 is then sent into a distillation column.

At the top of the column, a fluid flow of 0.103 l/h is drawn off whose composition by weight is as follows:

EB: Ethylbenzene 0.34%
PX: Paraxylene 1.8%
MX: Metaxylene 87.1%
OX: Orthoxylene 10.7%.

The flow rates that relate to the input of the distillation column and the crystallization are 1 and 0.55. The metaxylene yield of the crystallization that is carried out according to that of Example 1 is 64%.

The amount of paraxylene that is produced by the overall unit is 11 times greater than the amount of metaxylene, or respectively 0.66 l/h of paraxylene with 99.7% purity and 0.06 l/h of metaxylene with 99.0% purity.

At the bottom of said column, a fluid flow rate of 0.087 l/h is drawn off that can be sent into a crystallization unit at a temperature of −60° C. to produce orthoxylene with 98.5% purity, after a resuspension of orthoxylene crystals at −20° C. and washing by pure orthoxylene.

EXAMPLE 5

In this example, the feedstock of the following composition by weight:

EB: Ethylbenzene 5.6%
PX: Paraxylene 22.6%
MX: Metaxylene 49.9%
OX: Orthoxylene 21.9% undergoes a first distillation stage before entering the adsorption unit in a simulated moving bed. The feedstock flow rate is 4.98 l/h. The distillation stage has as its object to deplete of orthoxylene the flow that penetrates the adsorption unit. An orthoxylene-enriched flow of 1.94 l/h is drawn off at the bottom of the column. The flow that is drawn off at the bottom of the column is distilled in a second column for distilling xylenes. At the top, a flow rate of a flow that contains pure orthoxylene with 99% purity is recovered. The flow that exits at the top of the first column with a flow rate of 3.04 l/h is depleted of orthoxylene and has the following composition by weight:

EB: Ethylbenzene 6.7%
PX: Paraxylene 28.3%
MX: Metaxylene 60.1%
OX: Orthoxylene 4.9%.

This flow is directed to the adsorption unit. The separation of the paraxylene is carried out in the same pilot unit as the one that is described in Example 1 and that consists of 24 beds that are 1.1 meters in length and 0.021 m in diameter containing a barium-exchanged X zeolite. A raffinate (raffinate 2) and an intermediate raffinate are drawn off continuously. The configuration is 5 beds, 9 beds, 5 beds, 3 beds and 2 beds respectively in zones 1, 2, 3A, 3B and 4.

The operating conditions are as follows:

Entering flow: 3.04 $l.h^{-1}$

Solvent: 5.17 $l.h^{-1}$ of desorbent (99.06% of paradiethylbenzene and 0.94% of other $C_{10}$ aromatic hydrocarbons)

Extract: 3.03 $l.h^{-1}$

Intermediate raffinate (R1): 3.98 $l.h^{-1}$

Raffinate (R2): 1.2 $l.h^{-1}$

Recycling flow rate (in zone 1): 16.05 $l.h^{-1}$

The switching time of the valves (or period) is 70.8 seconds.

After paradiethylbenzene is distilled, the extract that is obtained and that is drawn off continuously delivers a flow of 0.83 l/h of paraxylene with 99.7% purity.

The 1.2 $l.h^{-1}$ of raffinate is distilled, and a fluid flow rate of 0.12 $l.h^{-1}$ is obtained whose composition by weight is as follows:

EB: Ethylbenzene 0.1%
PX: Paraxylene 1.9%
MX: Metaxylene 92.3%
OX: Orthoxylene 5.6%.

The metaxylene yield is 6%. The metaxylene yield of the crystallization that is produced according to that of Example 1 is 79%.

The amount of paraxylene that is produced by the overall unit is about 10 times greater than the amount of metaxylene that is produced, or respectively 0.83 l/h of paraxylene with 99.7% purity and 0.086 l/h of metaxylene with 99.0% purity.

EXAMPLE 6

It is desired to produce paraxylene with the strongest productivity possible and simultaneously metaxylene in an amount that is about fifteen times less. The pilot unit that is used to do this consists of 20 columns that are 1.1 m in length and 0.021 m in diameter. 344 g of barium-exchanged X zeolite with a moisture level of 5.5%, expressed in terms of fire loss at 900° C., is loaded per column. The operating temperature is 175° C., the pressure at the intake of the recycling pump is kept at 10 bar, all of the injected or drawn-off flows have the flow rate being monitored, with the exception of the intermediate raffinate that has the pressure being monitored; and the injection and draw-off flow rates are expressed in ambient pressure conditions and at 20° C. Four beds are counted between the injection of desorbent and draw-off of extract, 7 beds between the draw-off of extract and the injection of feedstock, 4 beds between the injection of feedstock and the draw-off of intermediate raffinate, 3 beds between the draw-off of intermediate raffinate and the draw-off of raffinate and 2 beds between the draw-off of raffinate and the injection of desorbent.

63 cm$^3$/min of feedstock with the following composition is injected:

Ethylbenzene 5.54%
Paraxylene 22.59%
Metaxylene 49.9%
Orthoxylene 21.97%.

78.75 cm$^3$/min of desorbent that consists of 98.9% of paradiethylbenzene and 0.7% of metadiethylbenzene are injected, whereby the difference at 100 consists of about ten components of C10 aromatic compounds.

38.5 cm$^3$/min of extract with the following composition by weight is drawn off:

Ethylbenzene 0.098%
Paraxylene 34.75%
Metaxylene 0.655%
Orthoxylene 2.87%
Paradiethylbenene 63.81%, whereby the difference at 100% consists of C10 aromatic compounds.

79.3 cm$^3$/min of intermediate raffinate is drawn off, whose composition by weight is:

Ethylbenzene 4.35%,
Paraxylene 0.94%,
Metaxylene 35.74%,
Orthoxylene 15.93%,
PDEB 42.73%, whereby the difference at 100% consists of C10 aromatic compounds.

23.95 cm$^3$/min of raffinate R2 is drawn off, whose composition by weight is:

Ethylbenzene 0.2%,
Paraxylene 0.44%,
Metaxylene 11.83%,
Orthoxylene 4.57%,
PDEB 82.68%, whereby the difference at 100% consists of C10 aromatic compounds.

The switching period is 60.7 seconds, and the flow rate of the recycling stream in zone 1 is 295.7 cm$^3$/min expressed at 50° C.

It is noted that in the extract, the purity of paraxylene is 97% for a yield of 94%. By contrast, relative to a market where the paraxylene would be produced with at least 99.6% purity with a yield of 96.6%, the solvent rate was reduced from 1.7 to 1.25, the productivity increased by 40%, and the absolute number of beds was reduced from 24 to 20.

The extract is distilled and sent into crystallization. The paraxylene crystals are separated from the mother liquor by centrifuging, resuspended, washed by molten, pure paraxylene and collected. Starting from paraxylene with 97% purity, paraxylene with a purity of approximately 99.6% will be obtained with 98% yield; for a crystallization temperature of −20°, the paraxylene content of the mother liquor will be about 38%. This mother liquor is recycled at the inlet of the adsorption column with the fresh feedstock.

Likewise, raffinate R2 is first distilled to recover the paradiethylbenzene. At the top of the column to be distilled, a mixture is obtained whose composition by weight is:

Ethylbenzene 0.11%,
Paraxylene 2.59%,
Metaxylene 70.18%,
Orthoxylene 27.12%.

This mixture is partially distilled before the crystallization zone to obtain at the top a metaxylene-enriched composition of the composition by weight:

Ethylbenzene 0.17%,
Paraxylene 3.08%,
Metaxylene 83.48%,
Orthoxylene 13.27%.

This mixture is subjected to a crystallization according to that of Example 1, and pure metaxylene at 99% with a yield of 55% is obtained.

The orthoxylene-enriched bottom fraction is recycled in the isomerization stage.

The preceding examples can be repeated with similar success by substituting the generically or specifically described reactants and/or operating conditions of this invention for those used in the preceding examples.

The entire disclosure of all applications, patents and publications, cited above and below, and of corresponding French Application No. 01/12.177, filed Sep. 20, 2001 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Process for co-production of paraxylene and metaxylene and/or orthoxylene from a feedstock that contains xylenes, ethylbenzene and C9–C10 hydrocarbons, whereby the process successively comprises:

A passage of feedstock (1) in a column (2) for distillation of xylenes from where a mixture (3) that comprises the majority of metaxylene, paraxylene, ethylbenzene and at least a portion of orthoxylene is drawn off at the top, and from where a flow (4) of C9–C10 hydrocarbons and the remaining portion of orthoxylene is drawn off at the bottom;

A separation of top mixture (3) in a simulated moving bed in at least one chromatographic column (9) containing a number of beds of an adsorbent that are interconnected in a closed loop and having a different selectivity for paraxylene, ethylbenzene, metaxylene and orthoxylene, whereby said column comprises at least five zones that are delimited by injections of mixture (3) (adsorption feedstock) and a desorbent (8) and draw-offs of an extract (10) that contains paraxylene, an intermediate fraction (11) that contains ethylbenzene, a raffinate (R2) (12) that contains orthoxylene and metaxylene, whereby a paraxylene desorption zone 1 is included between the injection of the desorbent and the sampling of the extract, whereby a zone 2 for desorption of ethylbenzene, orthoxylene and metaxylene is included between the sampling of the extract and the injection of the adsorption feedstock, whereby a zone 3A for paraxylene adsorption is included between the injection of the feedstock and the draw-off of the intermediate fraction, whereby a zone 3B for ethylbenzene adsorption is included between the draw-off of the intermediate fraction and the draw-off of raffinate (R2), and whereby a zone 4 is included between the draw-off of raffinate (R2) and the injection of desorbent, whereby the process is characterized in that Raffinate (2) is distilled to eliminate essentially all of the desorbent, and a distilled raffinate (18) is drawn off, The extract is distilled to recover a paraxylene-enriched fraction (16).

The process is also characterized in that:

Either distilled raffinate (18) is sent at least in part to at least one crystallization zone (27), and metaxylene with a purity of at least 99% is recovered, Or distilled raffinate (18) is sent at least in part into a second distillation zone (23), a top flow (24) that contains metaxylene and a bottom fraction (25) that contains orthoxylene (24) are recovered, the top flow is crystallized at least in part, metaxylene with a purity of at least 99% is recovered, and/or said bottom fraction is crystallized at least in part, and orthoxylene with a purity of at least 98.5% is recovered.

2. A process according to claim 1, in which flow (4) is distilled in a distillation column (5) to produce a high-purity orthoxylene flow (6) at the top and a flow (7) that contains C9–C10 hydrocarbons at the bottom.

3. A process according to one of claim 1, in which the crystallization of metaxylene and the crystallization of orthoxylene are carried out in a single crystallization zone, in runs, to produce metaxylene or orthoxylene separately.

4. A process according to one of claim 1, in which the crystallization of metaxylene and the crystallization of orthoxylene are carried out in separate crystallization zones.

5. A process according to one of claim 1, in which a portion of orthoxylene-enriched bottom fraction (25) is isomerized in at least one isomerization zone, and the isomerate that is obtained is recycled in distillation column (2).

6. A process according to one of claims 1, in which the adsorbent that is used in the separation stage is a barium-exchanged X zeolite or a potassium-exchanged Y zeolite or a barium- and potassium-exchanged Y zeolite.

7. A process according to one of claims 1, in which the desorbent is selected from among paradiethylbenzene, toluene, paradifluorobenzene or mixed with diethylbenzenes.

8. A process according to one of claims 1, in which the volumetric ratio of desorbent to adsorption feedstock is between 0.5 and 2.5.

9. A process according to claim 1, in which the separation stage is conducted at a temperature that is generally between 20° C. and 250° C., and under a pressure that is between the bubble pressure of xylenes at the operating temperature and 20 bar.

10. A process according to claim 1, in which to produce high-purity metaxylene, the flow rates of zones 3A and 3B as well as the distillation of orthoxylene in column (2) and/or second column (23) are regulated to obtain as a crystallization feedstock an effluent that is essentially free of ethylbenzene and desorbent, with a molar composition that is delimited by the four points: pure metaxylene, eutectic binary metaxylene-paraxylene (metaxylene 87.0%, paraxylene 13.0%), eutectic ternary meta-ortho-paraxylene (metaxylene 61.4%, orthoxylene 30.5%, paraxylene 8.1%), and eutectic binary meta-orthoxylene (metaxylene 66.6%, orthoxylene 33.4%).

11. A process according to claim 1, in which at least a portion of paraxylene-enriched fraction (16) feeds a crystallization batch vat to obtain, in runs, after passage into crystallization zone (27), a paraxylene flow (28) at at least 99.90%.

12. A process according to claim 1, in which to produce orthoxylene, the flow rates of zones 3A and 3B as well as the distillation of orthoxylene in column (2) and/or second column (23) are regulated to obtain as a crystallization feedstock an effluent that is essentially free of ethylbenzene and desorbent, with a molar composition that is delimited by the four pure orthoxylene points: eutectic binary orthoxylene-paraxylene (orthoxylene 75.7%, paraxylene 24.3%), eutectic ternary meta-ortho-paraxylene (metaxylene 61.4%, orthoxylene 30.5%, paraxylene 8.1%), and eutectic binary meta-orthoxylene (metaxylene 66.6%, orthoxylene 33.4%).

13. A process according to claim 1, in which the crystallization zone or zones comprise at least one crystallizer and in which a refrigeration unit is used to operate at a temperature of between −45° C. and −60° C. in the case where it is sought to produce metaxylene, between −20° C. and −60° C. in the case where it is sought to produce orthoxylene and between 20° C. and −50° C. in the case where it is sought to produce paraxylene and in which the mother liquor that is separated from the crystals is entrained to a storage vat after the crystallization stage to be recycled in the isomerization unit.

14. A process according to claim 1, in which the chromatographic column contains at least 24 beds, including at least 3 beds in zone 3B.

15. A process according to claim 1, in which fraction (16) is enriched with paraxylene at at least 50% purity and is sent into at least one crystallization zone to deliver paraxylene crystals and a mother liquor, the crystals are separated from the mother liquor, optionally resuspended, washed and recovered, and the mother liquor is recycled in the chromatographic column.

16. A process according to claim 8, wherein said volumetric ratio is between 1.4 and 1.7.

17. A process according to claim 9, wherein said temperature is between 90° C. and 210° C.

18. A process according to claim 9, wherein said temperature is between 160° C. and 200° C.

19. A process according to claim 1, wherein distilled raffinate (18) is sent at least in part to at least one crystallization zone (27), and metaxylene with a purity of at least 99% is recovered.

20. A process according to claim 1, wherein distilled raffinate (18) is sent at least in part into a second distillation zone (23), a top flow (24) that contains metaxylene and a bottom fraction (25) that contains orthoxylene (24) that contains metaxylene and a bottom fraction (25) that contains orthoxylene (24) are recovered, the top flow is crystallized at least in part, metaxylene with a purity of at least 99% is recovered, and/or said bottom fraction is crystallized at least in part, and orthoxylene with a purity of at least 98.5% is recovered.

* * * * *

UNITED STATES PATENT AND TRADEMARK OFFICE
CERTIFICATE OF CORRECTION

PATENT NO. : 6,841,714 B2
DATED : January 22, 2005
INVENTOR(S) : Philibert Leflaive et al.

It is certified that error appears in the above-identified patent and that said Letters Patent is hereby corrected as shown below:

Title page,
Item [75], Inventors, "Lyons," should read -- Lyon --.

Column 17,
Lines 28, 32 and 35, delete "one of ".
Lines 40, 44 and 48, delete "to one of claims 1" and insert -- claim 1 --.

Column 18,
Line 55, delete "(24) that contains metaxylene and a bottom fraction (25) that contains orthoxylene (24)".

Signed and Sealed this

Third Day of May, 2005

JON W. DUDAS
*Director of the United States Patent and Trademark Office*